US011718881B2

(12) United States Patent
Liu et al.

(10) Patent No.: US 11,718,881 B2
(45) Date of Patent: Aug. 8, 2023

(54) DETECTION REAGENT, DETECTION KIT AND DETECTION METHOD FOR ITGA4 GENE METHYLATION

(71) Applicant: CREATIVE BIOSCIENCES (GUANGZHOU) CO., LTD., Guangdong (CN)

(72) Inventors: Xianglin Liu, Guangdong (CN); Hongzhi Zou, Guangdong (CN)

(73) Assignee: CREATIVE BIOSCIENCES (GUANGZHOU) CO., LTD., Guangdong (CN)

( * ) Notice: Subject to any disclaimer, the term of this patent is extended or adjusted under 35 U.S.C. 154(b) by 429 days.

(21) Appl. No.: 16/603,451

(22) PCT Filed: Dec. 26, 2017

(86) PCT No.: PCT/CN2017/118563
§ 371 (c)(1),
(2) Date: Oct. 7, 2019

(87) PCT Pub. No.: WO2018/188377
PCT Pub. Date: Oct. 18, 2018

(65) Prior Publication Data
US 2020/0149116 A1    May 14, 2020

(30) Foreign Application Priority Data
Apr. 12, 2017  (CN) .......................... 201710236243.9

(51) Int. Cl.
*C12Q 1/6886* (2018.01)
*G01N 33/543* (2006.01)

(52) U.S. Cl.
CPC ..... *C12Q 1/6886* (2013.01); *G01N 33/54326* (2013.01)

(58) Field of Classification Search
None
See application file for complete search history.

(56) References Cited

U.S. PATENT DOCUMENTS

| 6,773,882 | B2 * | 8/2004 | Hogan | C12Q 1/6895 |
| | | | | 435/6.15 |
| 2010/0317000 | A1 | 12/2010 | Zhu | |
| 2013/0325360 | A1 * | 12/2013 | Deciu | G16B 30/10 |
| | | | | 702/20 |
| 2016/0040246 | A1 | 2/2016 | Ahlquist et al. | |
| 2019/0010557 | A1 | 1/2019 | Zou et al. | |

FOREIGN PATENT DOCUMENTS

| CN | 101353695 A | 1/2009 |
| CN | 105112529 A | 12/2015 |
| CN | 105543354 A | 5/2016 |
| CN | 105543378 A | 5/2016 |
| CN | 106947822 A | 7/2017 |
| WO | WO2013097868 A1 | 7/2013 |

OTHER PUBLICATIONS

Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
EESR of corresponding EP application EP17905728, Nov. 26, 2020, 9 pages.
First Office Action of corresponding CA application CA3058015, dated Sep. 3, 2020, 4 pages.
First Office Action of corresponding AU application AU2017409499, dated Feb. 15, 2021, 5 pages.
First Office Action of corresponding JP application JP2019555590, dated Apr. 3, 2020, with English translation, 9 pages.
First Office Action of corresponding KR application KR20197033100, dated Nov. 26, 2020, with English translation, 9 pages.
First Office Action of corresponding IN application IN201937043357, dated Mar. 23, 2021, 5 pages.
First Office Action of corresponding RU Application RU2019132049, dated Jun. 9, 2020, with English translation, 8 pages.
Christian Gerecke et al., "Hypermethylation of ITGA4, TFPI2 and VIMENTIN promoters is increased in inflamed colon tissue: putative risk markers for colitis-associated cancer," J Cancer Res Clin Oncol, Apr. 23, 2015, 14(12), pp. 2097-2107. Cited in EESR.
Eugene Chang et al., "Detection of colorectal neoplasm using promoter methylation of ITGA4, SFRP2, and p16 in stool samples: a preliminary report in Korean patients," Hepatogastroenterology 57, Jul. 31, 2010, pp. 720-727. Cited in 1st OA of corresponding KR application.
Hernán G. Hernández, et al., "Optimizing methodologies for PCR-based DNA methylation analysis," Biotechniques 55, Oct. 31, 2013, pp. 181-197. Cited in 1st OA of corresponding KR application.
Ahmed, D. et al. A Tissue-Based Comparative Effectiveness Analysis of Biomarkers for Early Detection of Colorectal Tumors. Clinical and Translational Gastroenterology., vol. 3, Dec. 6, 2012 (Dec. 6, 2012); e27; pp. 1-9.
Ausch, C. et al. Comparative Analysis of PCR-Based Biomarker Assay Methods for Colorectal Polyp Detection from Fecal DNA. Clinical Chemistry., vol. 55, No. 8,Dec. 31, 2009 (Dec. 31, 2009), pp. 1559 to 1563.

(Continued)

*Primary Examiner* — Katherine D Salmon
(74) *Attorney, Agent, or Firm* — Muncy, Geissler, Olds & Lowe, P.C.

(57) ABSTRACT

Provided are a detection kit and detection method for ITGA4 gene methylation. A primer and a probe provided by the present invention are matched, then detection can be carried out by taking a feces sample as an object, and thus the detection is simple, convenient and rapid. The detection can also be carried out on tissue specimens. Moreover, in the process of detecting the samples, the detection specificity and sensitivity are also improved. The experiment proves that for the feces specimen, when the specificity is 95.2%, the sensitivities of the methylated ITGA4 to intestinal cancer and adenoid tumor are 83.8% and 41.6%, respectively; and for the intestinal cancer tissue, when the specificity is 97.6% (40/41), the detection rates for colorectal cancer and adenoid tumor are 96.2% (101/105) and 71.6% (78/109), respectively. The effects are superior to the detection effects obtained by adopting other primers or probes.

4 Claims, 2 Drawing Sheets

Specification includes a Sequence Listing.

(56) References Cited

OTHER PUBLICATIONS

Park, J. et al. "Aberrant Methylation of Integrin α4 Gene in Human Gastric Cancer Cells". Oncogene., vol. 23, Mar. 1, 2004 (Mar. 1, 2004), pp. 3474 to 3480.
Sun Ning et al.; "Detection and Extraction of Free Methylated DNA in Urine by Applying Magnetic Bead Method", Journal of China Medical University, vol. 44; No. Oct. 10, 2015, pp. 897-900.

* cited by examiner

DETECTION REAGENT, DETECTION KIT AND DETECTION METHOD FOR ITGA4 GENE METHYLATION

The present application claims priority to the Chinese Patent Application No. 201710236243.9, entitled "Detection Reagent, Detection Kit and Detection Method for ITGA4 Gene Methylation", and filed to the Chinese Patent Office on Apr. 12, 2017, the entire contents of which are incorporated herein by reference.

TECHNICAL FIELD

The present invention relates to the technical field of gene detection, in particular to a detection reagent, a detection kit and a detection method for ITGA4 gene methylation.

BACKGROUND

The fecal immunochemical test for DNA (FIT-DNA) was included in the screening methods for colorectal cancer in 2016 by the United States Preventive Services Task Force (USPSTF). One of the principles of this test is to detect methylation levels of specific genes in exfoliated cells in feces. The selection of DNA methylation markers with very high sensitivity and specificity to intestinal cancer is the basis of this test. The current research shows that the detection of ITGA4 gene methylation has high detection sensitivity and specificity to intestinal cancer in tissue and feces specimens.

The research shows that the detection sensitivity of methylated ITGA4 to adenoid tumor in feces specimens is 69% (9/13) and the specificity is 79% (22/28). Another research shows that in detecting methylated ITGA4 in feces specimens, when the specificity is 100% (31/31), the detection rates for colorectal cancer and colorectal adenoid tumor are 36.7% (11/30) and 16% (4/25), respectively. These research results suggest that there is still great room for improvement of the detection sensitivity and specificity of this gene to intestinal cancer and adenoid tumor in feces specimens.

The key factor influencing the detection sensitivity and specificity of markers is the sequences of primers, thereby being of great importance to further relate to the detection primers with high sensitivity and specificity for ITGA4 gene methylation.

SUMMARY

To this end, the technical problem to be solved by the present invention is to provide a detection kit and a detection method for ITGA4 gene methylation. Both quantitative and qualitative kits provided by the present invention can achieve specificity and sensitivity detection for ITGA4 gene methylation.

The present invention provides:

a qualitative detection kit for ITGA4 gene methylation, which takes feces, tissue or cells as a sample to be detected and comprises an ITGA4 gene capturing reagent and an ITGA4 gene methylation qualitative detection reagent.

In an example of the present invention, the ITGA4 gene capturing reagent comprises a magnetic bead probe complex. In some specific examples, a sequence of the probe is shown as SEQ ID NO: 1.

The ITGA4 gene methylation qualitative detection reagent comprises a detection primer, and a nucleotide sequence of the detection primer is shown as SEQ ID NO: 2-3.

The present invention further provides a quantitative detection kit for ITGA4 gene methylation, which takes feces, tissue or cells as a sample to be detected and comprises an ITGA4 gene capturing reagent and an ITGA4 gene methylation quantitative detection reagent.

In an example of the present invention, the ITGA4 gene capturing reagent comprises a magnetic bead probe complex. In some specific examples, a sequence of the probe is shown as SEQ ID NO: 1.

In an example of the present invention, the ITGA4 gene methylation quantitative detection reagent comprises a detection primer and a detection probe, wherein a nucleotide sequence of the detection primer is shown as SEQ ID NO: 4-5; and a nucleotide sequence of the detection probe is shown as SEQ ID NO: 6.

The present invention further provides a detection kit for ITGA4 gene methylation, which takes feces, tissue or cells as a sample to be detected and comprises an ITGA4 gene capturing reagent, an ITGA4 gene methylation qualitative detection reagent and an ITGA4 gene methylation quantitative detection reagent.

The ITGA4 gene capturing reagent comprises a magnetic bead probe complex; in the magnetic bead probe complex, a nucleotide sequence of the probe is shown as SEQ ID NO: 1;

the ITGA4 gene methylation qualitative detection reagent comprises a detection primer; a nucleotide sequence of the detection primer is shown as SEQ ID NO: 2-3; and the ITGA4 gene methylation quantitative detection reagent comprises a detection primer and a detection probe; a nucleotide sequence of the detection primer is shown as SEQ ID NO: 4-5, and a nucleotide sequence of the detection probe is shown as SEQ ID NO: 6.

ITGA4 genes are captured in feces specimens by using a capturing sequence of the nucleotide sequence shown as SEQ ID NO: 1, and the methylation level of ITGA4 is detected in 240 feces specimens (80 cases of intestinal cancer, 77 cases of adenoid tumor larger than or equal to 1 cm, and 83 cases of normal). Results show that when the specificity is 95.2%, the sensitivities of methylated ITGA4 to intestinal cancer and adenoid tumor are 83.8% and 41.6%, respectively.

The methylation level of ITGA4 is detected in 105 pairs of paired intestinal cancer tissue, 109 cases of adenoid tumor tissue larger than or equal to 1 cm, and 41 cases of normal intestinal epithelial tissue by using the primer and the probe of the qMSP test. When the specificity is 97.6%, the detection rates for colorectal cancer and adenoid tumor are 96.2% and 71.6%, respectively.

The methylation level of ITGA4 genes is detected in six colorectal cancer cell lines including Widr, SW480, HCT15, HT29, Caco2 and DLD1 by using the primer of the MSP test. The result shows that ITGA4 is methylated in all the six colorectal cancer cells.

Preferably, the sample to be detected of the kit provided by the present invention is feces and/or tissue;

in some specific examples, the sample to be detected is feces.

The present invention further provides a qualitative detection method for ITGA4 gene methylation, comprising: by taking a sample to be detected as a template, capturing ITGA4 genes by a capturing reagent, and then modifying with bisulfite, amplifying with a qualitative detection reagent, and determining whether the ITGA4 genes are methylated or not according to an amplification product;

wherein the sample to be detected is feces, tissue or cells;

the capturing reagent comprises a magnetic bead probe complex; in the magnetic bead probe complex, a nucleotide sequence of the probe is shown as SEQ ID NO: 1;

the qualitative detection reagent comprises a detection primer; a nucleotide sequence of the detection primer is shown as SEQ ID NO: 2-3.

Specifically, by taking the sample to be detected as the template, capturing the ITGA4 genes by an ITGA4 gene capturing sequence of the nucleotide sequence shown as SEQ ID NO: 1, then treating and modifying by bisulfite, then amplifying carried out with an ITGA4 gene methylation qualitative detection primer of the nucleotide sequence shown as SEQ ID NO: 2-3, and determining whether the ITGA4 genes are methylated or not according to the amplification product; and the sample to be detected is feces, tissue or cells.

Preferably, the sample to be detected is feces, colorectal cancer, colorectal adenoid tumor, normal intestinal epithelial tissue or cell lines. Preferably, the sample to be detected is feces.

In a magnetic bead capturing method, magnetic beads are taken as a solid phase adsorption carrier, and a specially designed reagent system and an extraction procedure ("Detection and Extraction of Free Methylated DNA in Urine by Applying Magnetic Bead Method", *Journal of China Medical University*, 2015, (10)) are used.

In the present invention, the sequence is shown as SEQ ID NO. 1. The ITGA4 genes in feces may be extracted and enriched by means of magnetic bead capturing.

The feces may optionally be treated by: uniformly mixing the feces in a buffer solution, centrifuging, taking a supernatant into another test tube, adding magnetic beads with specific complementary oligonucleotide capturing sequences to the supernatant, after incubating and hybridizing, adsorbing the magnetic beads on one side of a tube wall by using a magnet, and after repeatedly washing, eluting target gene DNA by using the buffer solution. The target genes may be captured by the method, and the enrichment process lasts about 2 hours.

The captured DNA is treated and modified with bisulfite for subsequent fluorescence quantitative PCR detection.

Amplification system: nuclease-free water 10.5 µL, 2× enzyme reaction solution 12.5 µL, forward primer and reverse primer (5 µM concentration) 0.5 µL each, and DNA to be detected 1 µL, totaling 25 µL.

Amplification procedure: 95° C. 5 min, (95° C. 30 s, 64° C. 30 s, and 72° C. 30 s)×34 Cycles, 72° C. 5 min, and 37° C. 30 s.

According to the amplification result, if an amplification band occurs, the genes are methylated.

The present invention further provides a quantitative detection method for ITGA4 gene methylation, comprising:

by taking a sample to be detected as a template, capturing ITGA4 genes by a capturing reagent, then modifying with bisulfite, performing quantitative detection with a quantitative detection reagent, and determining the methylation level of the ITGA4 genes according to a quantitative result;

wherein the sample to be detected is feces, tissue or cells;

the capturing reagent comprises a magnetic bead probe complex; in the magnetic bead probe complex, a nucleotide sequence of the probe is shown as SEQ ID NO: 1;

the quantitative detection reagent comprises a detection primer and a detection probe; a nucleotide sequence of the detection primer is shown as SEQ ID NO: 4-5, and a nucleotide sequence of the detection probe is shown as SEQ ID NO: 6.

Specifically, by taking the sample to be detected as the template, capturing the ITGA4 genes by an ITGA4 gene capturing sequence of the nucleotide sequence shown as SEQ ID NO: 1, then treating and modifying by bisulfite, then quantitative detecting is carried out with an ITGA4 gene methylation quantitative detection primer of the nucleotide sequence shown as SEQ ID NO: 4-5 and an ITGA4 gene methylation quantitative detection probe of the nucleotide sequence shown as SEQ ID NO: 6, and the methylation level of the ITGA4 genes is determined according to the quantitative result; and the sample to be detected is feces, tissue or cells.

Preferably, the sample to be detected is feces, colorectal cancer, colorectal adenoid tumor, normal intestinal epithelial tissue or cell lines. Preferably, the sample to be detected is feces.

In a magnetic bead capturing method, magnetic beads are taken as a solid phase adsorption carrier, and a specially designed reagent system and an extraction procedure ("Detection and Extraction of Free Methylated DNA in Urine by Applying Magnetic Bead Method", *Journal of China Medical University* 2015, (10)) are used.

In the present invention, the sequence is shown as SEQ ID NO. 1. The ITGA4 genes in feces may be extracted and enriched by means of magnetic bead capturing.

The feces may optionally be treated by: uniformly mixing the feces in a buffer solution, centrifuging, taking a supernatant into another test tube, adding magnetic beads with specific complementary oligonucleotide capturing sequences to the supernatant, after incubating and hybridizing, adsorbing the magnetic beads on one side of a tube wall by using a magnet, and after repeatedly washing, eluting target gene DNA by using the buffer solution. The target genes may be captured by the method, and the enrichment process lasts about 2 hours.

The captured DNA is treated and modified with bisulfite for subsequent fluorescence quantitative PCR detection.

The amplification reaction system: nuclease-free water 8.2 µL, 5× enzyme reaction buffer solution 5 µL, $MgCl_2$ (25 mM) 5 µL, dNTPs (10 mM) 1 µL, reaction enzyme 0.5 µL, a forward primer (100 µM) 0.125 µL, a backward primer (100 µM) 0.125 µL, a probe (100 µM) 0.05 µL, and DNA to be detected 5 µL, totaling 25 µL.

The procedure: 95° C. 4 min, (95° C. 20 s, 56° C. 30 s, and 72° C. 30 s)×45 Cycles, and 37° C. 30 s.

According to the quantitative result, the relative methylation level of the ITGA4 genes is obtained through calculation by taking an ACTB gene as a reference gene.

The primer and the probe provided by the present invention are matched, then detection can be carried out on a feces sample, and thus the detection is simple, convenient and rapid. In the present invention, the detection can also be carried out on tissue specimens. Moreover, in the process of detecting the samples, the detection specificity and sensitivity are also improved. The experiment proves that for the feces specimen, when the specificity is 95.2%, the sensitivities of the methylated ITGA4 to intestinal cancer and adenoid tumor are 83.8% and 41.6%, respectively; and for the intestinal cancer tissue, when the specificity is 97.6% (40/41), the detection rates for colorectal cancer and adenoid tumor are 96.2% (101/105) and 71.6% (78/109), respectively. The effects are superior to the detection effects obtained by adopting other primers or probes.

DETAILED DESCRIPTION

The present invention provides a detection reagent, a detection kit and a detection method for ITGA4 gene methylation, which can be achieved by a person skilled in the art by referring to the contents herein and appropriately improving process parameters. It is specifically noted that all similar substitutes and modifications apparent to a person skilled in the art are deemed to be included in the present invention. The methods and applications of the present invention have been described through preferred examples, and it will be apparent to a person skilled in the art that the technology of the present invention may be practiced and applied with modification or appropriate alteration and combination of the methods and applications herein, without departing from the contents, spirit and scope of the present invention.

The test materials, reagents and instruments used in the present invention are all common commercial products and can be purchased in the market.

The present invention is further illustrated by the following examples:

Example 1 Qualitative Detection

Six colorectal cancer cell lines including Widr, SW480, HCT15, HT29, Caco2 and DLD1 were selected, and healthy cells CCD-18CO were additionally used as a control. The MSP test was used to detect whether ITGA4 genes were methylated in these cells; and each cell line was repeatedly detected 10 times.

The method comprises the following steps:

1. Cell pellets were collected and transferred to a new 15 mL centrifuge tube previously containing 3 mL of cell lysate.

100 μL of capturing magnetic beads were added to the centrifuge tube, wherein the capturing magnetic beads contain capturing sequences (5'-TGCTTCTCCGGGTACGGGCCGCT GGGTGGGGTC-3) of the sequence shown as the capturing sequence SEQ ID NO: 1. The mixture was subjected to incubation in a water bath kettle at 92° C. for 10 min and on a room temperature shaker at 100 rpm for 1 h, and then placed on a magnetic stand for 5 min after short centrifugation, with a supernatant removed.

500 μL of a washing solution was added to the 15 mL centrifuge tube, oscillated and shaken to enable magnetic beads on a wall of the tube to be completely suspended, and transferred into a new 2 mL centrifuge tube after short centrifugation. The mixture was subjected to incubation in a room temperature dry bath incubator at 900 rpm for 1 min and then placed on the magnetic stand for 1 min, with a supernatant removed. The process was repeated 4 times.

55 μL of an eluent was added, shortly centrifuged, incubated in the dry bath incubator at 92° C. and at 900 rpm for 10 min, shortly centrifuged, placed on the magnetic stand, and transferred into a new EP tube within 3 min.

2. Bisulfite transformation was carried out with EZ DNA methylation Kit (ZYMO RESEARCH).

3. Amplification: primers including:

```
Upstream primer sequence:
                                (SEQ ID NO: 2)
5'-TCGGAGAAGTAGCGCGAGTATTC-3'

Downstream primer sequence:
                                (SEQ ID NO: 3)
5'-AAATCGACCCACCGCGAACG-3'
```

System: 25 μL (1× system: nuclease-free water 10.5 μL, GoTaq Hot Start Colorless Master Mix 12.5 μL, Forward primer and Reverse primer (concentration 5 uM) 0.5 μL each, and DNA to be detected 1 μL)

Procedure: 95° C. 5 min, (95° C. 30 s, 64° C. 30 s, and 72° C. 30 s)×34 Cycles, 72° C. 5 min, and 37° C. 30 s.

4. Amplification result observation.

According to the amplification result, agarose gel electrophoresis is carried out on a PCR product, and if bands occur, methylation occurs.

Results: the methylation of ITGA4 was detected in all the six intestinal cancer cells, with the accuracy of 10-repeated detection up to 100%, while the methylation was not detected in the healthy cells.

Example 2 Quantitative Detection

1. Feces as Sample 240 feces specimens were selected, including 80 cases of intestinal cancer, 77 cases of adenoid tumor larger than or equal to 1 cm, and 83 cases of normal, based on enteroscopy, and quantitative detection of the methylation level of ITGA4 genes was carried out.

Test process: ITGA4 genes were captured by using a capturing sequence (SEQ ID NO: 1) in the feces specimens; and the capturing conditions and process were the same as those in Example 1), and quantitative detection of the methylation level of the ITGA4 genes in the specimens was carried out through the qMSP test by using ACTB as a reference gene.

Quantitative detection primers and probes:

```
Upstream primer sequence:
                                (SEQ ID NO: 4)
5'-ACGCGAGTTTTGCGTAGTC-3'

Downstream primer sequence:
                                (SEQ ID NO: 5)
5'-TCCGAATACGAACCGCTAA-3'
```

-continued

Detection probe sequence:
(SEQ ID NO: 6)
5'-ACGGAGTTCGGTTTTGCGTTTTC-3'

System: 25 μL (1× system: nuclease-free water 8.2 μL, 5× Colorless GoTaq Flexi Buffer 5 μL, MgCl$_2$ (25 mM) 5 μL, dNTPs (10 mM) 1 μL, GoTaq Hot Start polymerase 0.5 μL, Forward primer (100 uM) 0.125 μL, Reverse primer (100 μM) 0.125 μL, Probe (100 μM) 0.05 μL, and DNA 5 μL)

Procedure: 95° C. 4 min, (95° C. 20 s, 56° C. 30 s, and 72° C. 30 s)×45 Cycles, and 37° C. 30 s.

Figure 1:
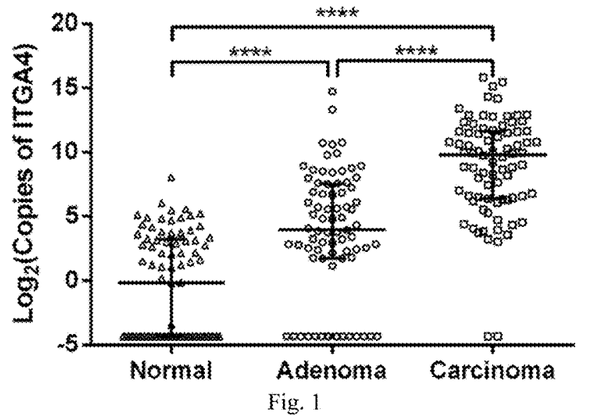
FIG. 1 shows a dot plot of methylation levels of ITGA4 genes in cancer, adenoid tumor and a normal group, wherein **** indicates that P is less than 0.0001.
Figure 2:
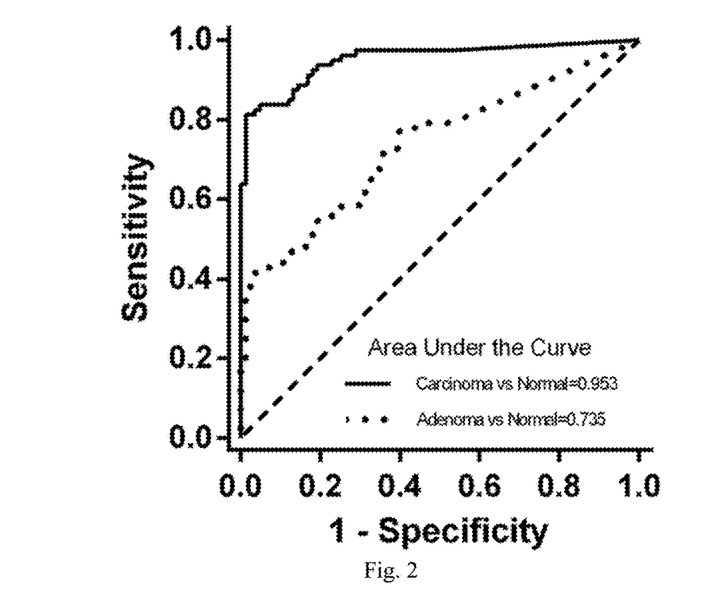
FIG. 2 shows an ROC graph, wherein AUC (cancer vs normal) is equal to 0.953 (95% CI: 0.920-0.985); and AUC (adenoid tumor vs normal) is equal to 0.735 (95% CI: 0.657-0.814)

In 240 feces specimens (80 cases of intestinal cancer, 77 cases of adenoid tumor larger than or equal to 1 cm, and 83 cases of normal), the methylation level of ITGA4 was detected, and the result showed that when the specificity is 95.2%, the sensitivities of the methylated ITGA4 to intestinal cancer and adenoid tumor were 83.8% and 41.6%, respectively (FIG. 1-2).

2. Tissue as Sample

Colorectal cancer, colorectal adenoid tumor and normal intestinal epithelial tissue specimens excised surgically or endoscopically were selected, and quantitative detection of the methylation level of ITGA4 genes was carried out, with the specimens including: 105 pairs of intestinal cancer and paracancerous paired tissue, 109 cases of adenoid tumor tissue larger than or equal to 1 cm, and 41 cases of normal intestinal epithelial tissue.

The DNA of each tissue was extracted and treated and modified with bisulfite, and then quantitative detection of the methylation level of ITGA4 genes in the specimens was carried out through the qMSP test.

An ROC curve (FIG. 2) was plotted according to the quantitative result, and the result showed: when the specificity was 97.6% (40/41), the detection rates for colorectal cancer and adenoid tumor were 96.2% (101/105) and 71.6% (78/109), respectively. The areas under the curve are respectively as follows: 0.958 (95% CI: 0.909-1) and 0.832 (95% CI: 0.761-0.902), (P of both is less than 0.001).

Example 3 Detection Limit

Figure 3:
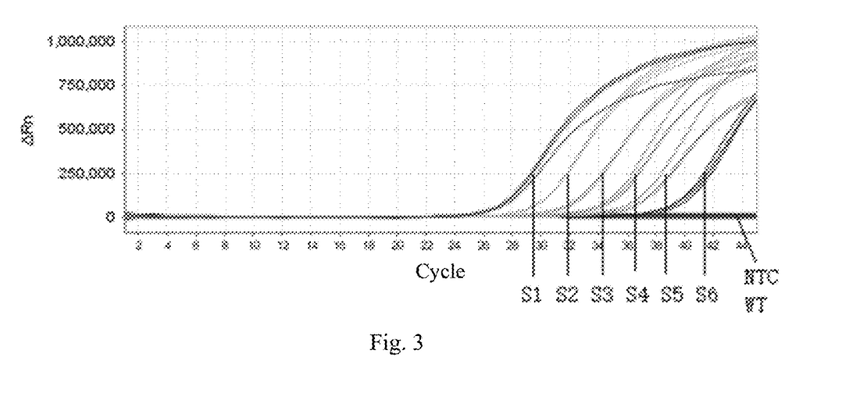
FIG. 3 shows an amplification curve of a gradiently diluted S1-S6 and a standard curve constructed therefrom, wherein NTC represents a non-template control, WT represents wild-type DNA as a control, and each sample is provided with three complex holes.
Figure 4:
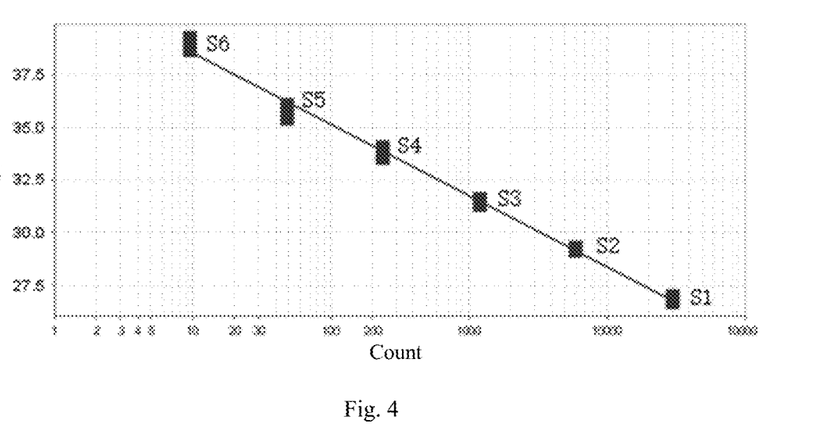
FIG. 4 shows the standard curve with linearity $R^2$ being equal to 0.995 and amplification efficiency being equal to 97.96%.

Bisulfite transformation was carried out by using CpGenomeUniversal Methylated DNA (purchased from Millipore) to obtain 20 ng/μL template DNA, and S1, S2, S3, S4, S5 and S6 were obtained by 5-fold gradient dilutions, with the concentrations of 20 ng/μL, 4 ng/μL, 0.8 ng/μL, 0.16 ng/μL, 0.032 ng/μL and 0.0064 ng/μL, respectively.

qPCR was carried out with a loading template amount of 5 μL (the method and the primer are same as those in Example 2). It can be seen that the actual DNA addition amounts of S1-S6 are 100 ng, 20 ng, 4 ng, 0.8 ng, 0.16 ng, and 0.032 ng, respectively. The qPCR result showed that the amount of DNA detectable by the gene primer probe ranged from 0.032 ng to 100 ng (FIG. 3).

Comparative Example 1

Bisulfite transformation was carried out by using CpGenomeUniversal Methylated DNA (purchased from Millipore); and ACTB was used as a reference gene, and then different primers and probes were used for quantitative detection to investigate the amplification effect of each set of probes and primers.

The primers and probes used were shown in Table 1:

TABLE 1

Primers and probes

| Name | Type | Sequence | Serial number | Ct value |
|---|---|---|---|---|
| Set 1 | Upstream primer | ACGCGAGTTTTGCGTAGTC | SEQ ID NO: 4 | 31.5 |
| | Downstream primer | TCCGAATACGAACCGCTAA | SEQ ID NO: 5 | |
| | Probe | ACGGAGTTCGGTTTTGCGTTTTC | SEQ ID NO: 6 | |
| Set 2 | Upstream primer | GTTTTCGTATTACGTTCGGG | SEQ ID NO: 7 | 31.7 |
| | Downstream primer | TCGAACCGACCTAAAATACC | SEQ ID NO: 8 | |
| | Probe | AATCGGGAGTGGGGTCGGGCGA | SEQ ID NO: 9 | |
| Set 3 | Upstream primer | TATCGAGAGCGTATGGTTTG | SEQ ID NO: 10 | 31.6 |
| | Downstream primer | CCACGTTATAAAAACGACCG | SEQ ID NO: 11 | |
| | Probe | AGGGTCGTCGTTCGGGAGACGGT | SEQ ID NO: 12 | |
| Set 4 | Upstream primer | AGAGTTATTTCGCGTTTTGC | SEQ ID NO: 13 | 31.7 |
| | Downstream primer | ATCCCGAACGTAATACGAAA | SEQ ID NO: 14 | |
| | Probe | TGGGAGGTTCGGGTTAGGACGCGA | SEQ ID NO: 15 | |
| Set 5 | Upstream primer | TGCGTTTTCGTATTACGTTC | SEQ ID NO: 16 | 33.3 |
| | Downstream primer | CCAACCGAAAACTTCGAATA | SEQ ID NO: 17 | |
| | Probe | GCGGTTCGTATTCGGAGAAGTAGCGCC | SEQ ID NO: 18 | |
| Set 6 | Upstream primer | GCGGTTCGTATTCGGAGAAG | SEQ ID NO: 19 | 35.8 |
| | Downstream primer | TCTACCGCCAACCGAAAACT | SEQ ID NO: 20 | |
| | Probe | AGCGCGAGTATTC | SEQ ID NO: 21 | |
| Set 7 | Upstream primer | TGCGGAGGCGTAGGGTC | SEQ ID NO: 22 | 32.8 |
| | Downstream primer | CAACCGAAATTCCCCAACG | SEQ ID NO: 23 | |
| | Probe | CCTACAACCGCGCGTAAACAAAACG | SEQ ID NO: 24 | |

Figure 5:
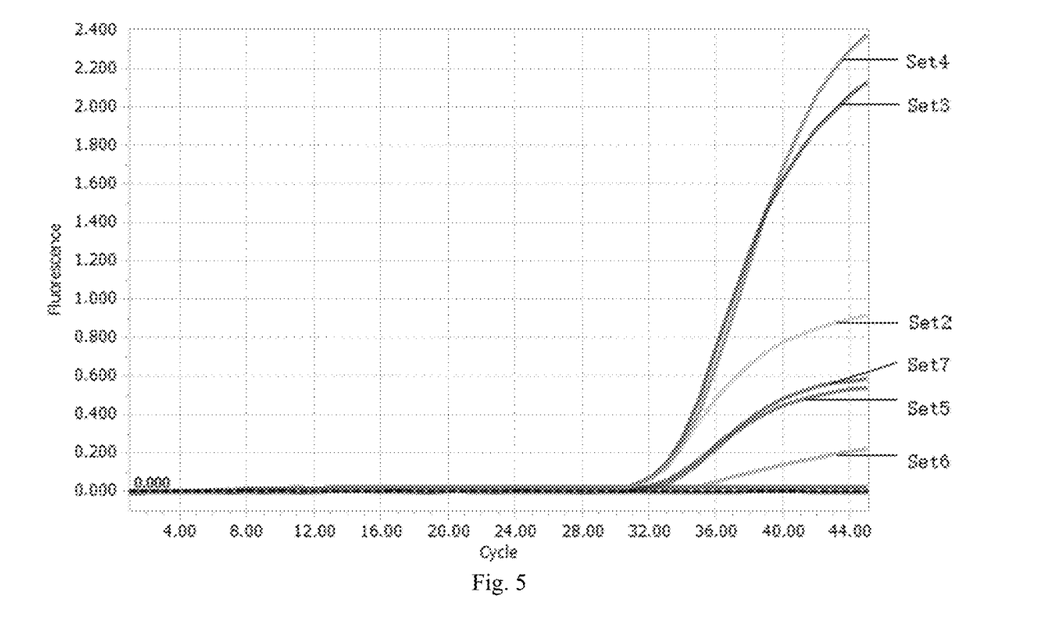
FIG. 5 shows amplification curves for different primers and probes.

The amplification results of each set of probes and primers were shown in FIG. 5, and the amplification result of Set 1 referred to the detection limit results of Example 3 (the detection template of S3 in the detection limit was the same as the detection template in this comparative example). As can be seen from the data in the table, in the specific amplification process aiming at the target gene, the amplification result Ct of the Set 1 was minimum, which showed the best amplification effect, and was superior to the probes of other sets.

The above are only preferred embodiments of the present invention. It should be noted that numerous modifications and adaptations may be made by one of ordinary skill in the art without departing from the principles of the present invention, and such modifications and adaptations are to be considered within the protection scope of the present invention.

The invention claimed is:

1. A colorectal cancer detection kit for use on excrement sample, comprising:
   an ITGA4 gene capturing reagent, comprising a magnetic bead probe complex; and
   an ITGA4 gene methylation detection reagent, comprising:
     a primer pair of nucleotide sequences consisting of SEQ ID NO: 4 and SEQ ID NO:5 respectively; and
     a probe consisting of SEQ ID NO: 6.

2. The detection kit according to claim 1, wherein the magnetic bead probe complex further comprises a probe consisting of SEQ ID NO: 1.

3. The detection kit according to claim 1, wherein the ITGA4 gene methylation detection reagent further comprises a primer pair of nucleotide sequences consisting of SEQ ID NO: 2 and SEQ ID NO:3 respectively.

4. A method of detecting ITGA4 gene methylation in at least one sample selected from a group consisting of feces, tissue or cells, comprising amplifying DNA extracted from said sample and detecting the presence of said ITGA4 gene methylation in said DNA by using the detection kit of claim 1.

* * * * *

SEQUENCE LISTING

<160> NUMBER OF SEQ ID NOS: 24

<210> SEQ ID NO 1
<211> LENGTH: 33
<212> TYPE: DNA
<213> ORGANISM: Artificial sequence
<220> FEATURE:
<223> OTHER INFORMATION: capturing sequence

<400> SEQUENCE: 1
tgcttctccg ggtacgggcc gctgggtggg gtc    33

<210> SEQ ID NO 2
<211> LENGTH: 23
<212> TYPE: DNA
<213> ORGANISM: Artificial sequence
<220> FEATURE:
<223> OTHER INFORMATION: Upstream primer of ITGA4

<400> SEQUENCE: 2
tcggagaagt agcgcgagta ttc    23

<210> SEQ ID NO 3
<211> LENGTH: 20
<212> TYPE: DNA
<213> ORGANISM: Artificial sequence
<220> FEATURE:
<223> OTHER INFORMATION: Downstream primer of ITGA4

<400> SEQUENCE: 3
aaatcgaccc accgcgaacg    20

<210> SEQ ID NO 4
<211> LENGTH: 19
<212> TYPE: DNA
<213> ORGANISM: Artificial sequence
<220> FEATURE:
<223> OTHER INFORMATION: Upstream primer of Set 1

<400> SEQUENCE: 4
acgcgagttt tgcgtagtc    19

<210> SEQ ID NO 5
<211> LENGTH: 19
<212> TYPE: DNA
<213> ORGANISM: Artificial sequence
<220> FEATURE:
<223> OTHER INFORMATION: Downstream primer of Set 1

<400> SEQUENCE: 5
tccgaatacg aaccgctaa    19

<210> SEQ ID NO 6
<211> LENGTH: 23
<212> TYPE: DNA
<213> ORGANISM: Artificial sequence

```
<220> FEATURE:
<223> OTHER INFORMATION: Probe of Set 1

<400> SEQUENCE: 6
acggagttcg gttttgcgtt ttc                                              23

<210> SEQ ID NO 7
<211> LENGTH: 20
<212> TYPE: DNA
<213> ORGANISM: Artificial sequence
<220> FEATURE:
<223> OTHER INFORMATION: Upstream primer of Set 2

<400> SEQUENCE: 7
gttttcgtat tacgttcggg                                                  20

<210> SEQ ID NO 8
<211> LENGTH: 20
<212> TYPE: DNA
<213> ORGANISM: Artificial sequence
<220> FEATURE:
<223> OTHER INFORMATION: Downstream primer of Set 2

<400> SEQUENCE: 8
tcgaaccgac ctaaaatacc                                                  20

<210> SEQ ID NO 9
<211> LENGTH: 22
<212> TYPE: DNA
<213> ORGANISM: Artificial sequence
<220> FEATURE:
<223> OTHER INFORMATION: Probe of Set 2

<400> SEQUENCE: 9
aatcgggagt ggggtcgggc ga                                               22

<210> SEQ ID NO 10
<211> LENGTH: 20
<212> TYPE: DNA
<213> ORGANISM: Artificial sequence
<220> FEATURE:
<223> OTHER INFORMATION: Upstream primer of Set 3

<400> SEQUENCE: 10
tatcgagagc gtatggtttg                                                  20

<210> SEQ ID NO 11
<211> LENGTH: 20
<212> TYPE: DNA
<213> ORGANISM: Artificial sequence
<220> FEATURE:
<223> OTHER INFORMATION: Downstream primer of Set 3

<400> SEQUENCE: 11
ccacgttata aaaacgaccg                                                  20

<210> SEQ ID NO 12
<211> LENGTH: 23
<212> TYPE: DNA
<213> ORGANISM: artificial sequence
<220> FEATURE:
<223> OTHER INFORMATION: Probe of Set 3

<400> SEQUENCE: 12
agggtcgtcg ttcgggagac ggt                                              23
```

-continued

```
<210> SEQ ID NO 13
<211> LENGTH: 20
<212> TYPE: DNA
<213> ORGANISM: Artificial sequence
<220> FEATURE:
<223> OTHER INFORMATION: Upstream primer of Set 4

<400> SEQUENCE: 13
agagttattt cgcgttttgc                                              20

<210> SEQ ID NO 14
<211> LENGTH: 20
<212> TYPE: DNA
<213> ORGANISM: Artificial sequence
<220> FEATURE:
<223> OTHER INFORMATION: Downstream primer of Set 4

<400> SEQUENCE: 14
atcccgaacg taatacgaaa                                              20

<210> SEQ ID NO 15
<211> LENGTH: 24
<212> TYPE: DNA
<213> ORGANISM: Artificial sequence
<220> FEATURE:
<223> OTHER INFORMATION: Probe of Set 4

<400> SEQUENCE: 15
tgggaggttc gggttaggac gcga                                         24

<210> SEQ ID NO 16
<211> LENGTH: 20
<212> TYPE: DNA
<213> ORGANISM: Artificial sequence
<220> FEATURE:
<223> OTHER INFORMATION: Upstream primer of Set 5

<400> SEQUENCE: 16
tgcgttttcg tattacgttc                                              20

<210> SEQ ID NO 17
<211> LENGTH: 20
<212> TYPE: DNA
<213> ORGANISM: Artificial sequence
<220> FEATURE:
<223> OTHER INFORMATION: Downstream primer of Set 5

<400> SEQUENCE: 17
ccaaccgaaa acttcgaata                                              20

<210> SEQ ID NO 18
<211> LENGTH: 27
<212> TYPE: DNA
<213> ORGANISM: Artificial sequence
<220> FEATURE:
<223> OTHER INFORMATION: Probe of Set 5

<400> SEQUENCE: 18
gcggttcgta ttcggagaag tagcgcg                                      27

<210> SEQ ID NO 19
<211> LENGTH: 20
<212> TYPE: DNA
<213> ORGANISM: Artificial sequence
<220> FEATURE:
<223> OTHER INFORMATION: Upstream primer of Set 6
```

```
<400> SEQUENCE: 19
gcggttcgta ttcggagaag                                              20

<210> SEQ ID NO 20
<211> LENGTH: 20
<212> TYPE: DNA
<213> ORGANISM: Artificial sequence
<220> FEATURE:
<223> OTHER INFORMATION: Downstream primer of Set 6

<400> SEQUENCE: 20
tctaccgcca accgaaaact                                              20

<210> SEQ ID NO 21
<211> LENGTH: 13
<212> TYPE: DNA
<213> ORGANISM: Artificial sequence
<220> FEATURE:
<223> OTHER INFORMATION: Probe of Set 6

<400> SEQUENCE: 21
agcgcgagta ttc                                                     13

<210> SEQ ID NO 22
<211> LENGTH: 17
<212> TYPE: DNA
<213> ORGANISM: Artificial sequence
<220> FEATURE:
<223> OTHER INFORMATION: Upstream primer of Set 7

<400> SEQUENCE: 22
tgcggaggcg tagggtc                                                 17

<210> SEQ ID NO 23
<211> LENGTH: 19
<212> TYPE: DNA
<213> ORGANISM: Artificial sequence
<220> FEATURE:
<223> OTHER INFORMATION: Downstream primer of Set 7

<400> SEQUENCE: 23
caaccgaaat tccccaacg                                               19

<210> SEQ ID NO 24
<211> LENGTH: 26
<212> TYPE: DNA
<213> ORGANISM: Artificial sequence
<220> FEATURE:
<223> OTHER INFORMATION: Probe of Set 7

<400> SEQUENCE: 24
cctacaaccg cgcgtaaaca aaaacg                                       26
```